United States Patent [19]

Sleigh et al.

[11] Patent Number: 5,418,226
[45] Date of Patent: May 23, 1995

[54] MONOQUATERNARY 2,16-BISPIPERIDINYLANDROSTANE DERIVATIVES

[75] Inventors: Thomas Sleigh, Wishaw; Ian C. Carlyle, Hamilton; Alan W. Muir, Ravenstruther, all of Scotland

[73] Assignee: Akzo N.V., Arnhem, Netherlands

[21] Appl. No.: 48,539

[22] Filed: Apr. 14, 1993

[30] Foreign Application Priority Data

Apr. 22, 1992 [EP] European Pat. Off. ............ 92303612

[51] Int. Cl.[6] .................... A61K 31/58; C07J 43/00
[52] U.S. Cl. ...................................... 514/176; 540/95
[58] Field of Search ......................... 540/95; 514/176

[56] References Cited

U.S. PATENT DOCUMENTS 3,553,212  1/1971  Hewett et al. ................ 260/239.5

Primary Examiner—Nicholas Rizzo
Attorney, Agent, or Firm—Mary E. Gormley; William M. Blackstone

[57] ABSTRACT

Monoquaternary 2,16-bispiperidinylandrostane neuromuscular blocking derivatives having the formula:

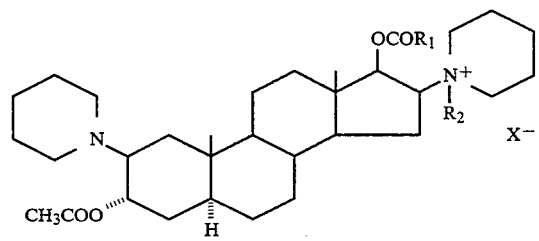

wherein
$R_1$ is ethyl;
$R_2$ is methyl or allyl; and
$X^-$ is a pharmaceutically acceptable anion; or pharmaceutically acceptable salts thereof.

5 Claims, No Drawings

MONOQUATERNARY 2,16-BISPIPERIDINYLANDROSTANE DERIVATIVES

The invention relates to monoquaternary 2,16-bis-piperidinylandrostane derivatives, a process for the preparation thereof, as well as a use for manufacturing a medicament containing the same, and to a method of neuromuscular blockade in patients.

In clinical anaesthesia the ideal neuromuscular blocking agent should cause non-depolarizing neuromuscular blockade of a fast onset, short duration and short recovery rate (see e.g. L. H. D. J. Booij and J. F. Crul, Clinical Experiences with Norcuron, ed. S. Agoston et al., Current Practice Series, Vol 11, Amsterdam, Excerpta Medica, 1983, p. 3–8). Such an agent is required for 'crash' intubation during emergency procedures in unfasted patients. Up to now, the only drug having a sufficiently fast onset time and short duration, is the depolarizing neuromuscular blocking agent suxamethonium. The blocking effects of suxamethonium, however, are often associated with side-effects, many of which are linked with its depolarizing mechanism of action.

The present invention gives a solution for the problem to find a drug having short onset, duration, and recovery times, and nevertheless, having a non-polarizing mechanism of action. Monoquaternary 2,16-bis-piperidinylandrostane derivatives having the formula:

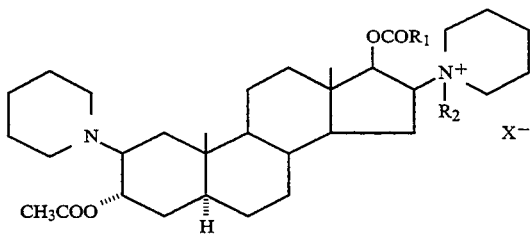

wherein
$R_1$ is ethyl;
$R_2$ is methyl or allyl; and
$X^-$ is a pharmaceutically acceptable anion; or pharmaceutically acceptable salts thereof, are found to have the desired properties.

Related neuromuscular blocking agents are known. The most pertinent compounds are pancuronium bromide and vecuronium bromide, which are commercially available as Pavulon ® and Norcuron ® respectively, and are disclosed in EP 8824 and U.S. Pat. No. 3,553,212 respectively. In contrast to pancuronium bromide, however, the present compounds are monoquaternary rather than bisquaternary compounds, and in comparison with vecuronium bromide the 17 substituent is a propionyl instead of an acetyl ester.

The search for non-depolarizing neuromuscular blocking agents having short onset, recovery and duration times, is seriously hampered by a generally observed phenomenon, i.e. that decrease of onset, recovery and duration times is associated with compounds of low potency (see for example W. C. Bowman et al., Anesthesiology (1988), 69, 57–62). Compounds having really short onset times, therefore, normally have such low potency that practical clinical use is excluded. For instance, a compound described by Muir et al., Anesthesiology (1989), 70, 533–540, having the structure of formula I wherein $R_1$ is propyl and $R_2$ is allyl (Org 7617), combines a short onset time with an extremely low potency. The potency was determined in the cat, but unpublished clinical data in humans confirmed the low potency of this compound in man. Compounds of this type, thus, are only active in patients when used in extremely high dosages, which give rise to unacceptable side-effects such as hypotensive action. This reference, therefore, teaches away from the present invention.

The compounds of the present invention show a drastically improved onset time in comparison with pancuronium bromide and vecuronium bromide. Also the recovery and duration times are considerably shorter. In cats, the potency of the compounds of the present invention is as unfavourably low as that of Org 7617 of the Muir et al. reference. Surprisingly, however, the potency of the compounds of this invention in humans is 2.5 to 4.5 times better than could be expected from the cat data. The improvement of the present compounds is regarded as clinically highly significant in terms of the predicted short time to intubation and rapid recovery of spontaneous breathing, without the occurence of hypotensive effects. Since the compounds possess a non-depolarizing action, other side-effects, similar to those associated with the depolarizing action of suxamethonium, will also be absent in man.

An important additional advantage of the compounds of this invention is the ease with which they can be reversed by anti-cholinesterase agents. By administration of edrophonium and, in particular, neostigmine the duration of action can be more effectively shortened than that of vecuronium bromide, which is important since it facilitates the early reversal of neuromuscular block in patients who cannot be intubated.

Another advantage of the present compounds is that they do not block re-uptake of the neurotransmitter noradrenaline into sympathetic nerve terminals, whereas many other muscle relaxants, including pancuronium bromide, possess this effect, which can cause elevation of both blood pressure and heart rate in man.

The compounds of this invention are particularly useful to replace suxamethonium for rapid sequence intubation and for ultra short surgical procedures which require the use of muscle relaxants.

Preferred compounds of the invention are the monoquaternary 2,16-bispiperidinylandrostane derivatives wherein $R_2$ is allyl, or pharmaceutically acceptable salts thereof.

The pharmaceutically acceptable anion $X^-$ is an anion derived from an organic or inorganic acid such as HCl, HBr, HI, $H_2SO_4$, $H_3PO_4$, acetic acid, propionic acid, glycolic acid, maleic acid, malonic acid, methanesulphonic acid, fumaric acid, succinic acid, tartaric acid, citric acid, benzoic acid, and ascorbic acid. Preferably $X^-$ is $Br^-$.

The compounds of formula I may be prepared by methods which are used for the preparation of analogous compounds. Suitable methods are described in the previously mentioned EP 8824 and U.S. Pat. No. 3,553,212, which methods are included by reference.

Preferably asteroid of the formula II:

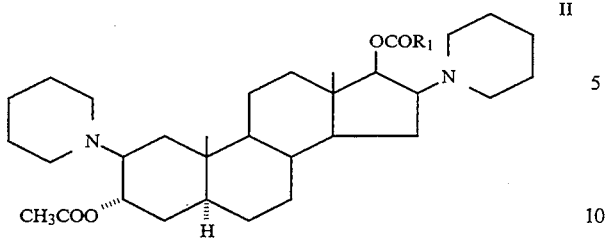

is reacted with $CH_2=CH-CH_2-L$ or $CH_3-L$, wherein $R_1$ has the previously defined meaning and L denotes a suitable leaving group, after which when L is not X, the group X is introduced, and the compound thus obtained is optionally converted into a pharmaceutically acceptable salt.

Suitable leaving groups L are halogens (preferably chlorine, bromine or iodine) and sulphonyloxy derivatives such as the p-toluenesulphonyloxy and the methanesulphonyloxy groups. Preferably the stefoid of formula II is reacted with allyl bromide or methyl bromide (for preparing the compounds of formula I having respectively $R_2$ is allyl or methyl). When L is not X, the anion $L^-$ thus formed can be replaced by $X^-$ by methods known in the art, among which are ion exchange, acid treatment or heavy metal treatment followed by acid treatment.

The novel compounds of formula I may be isolated from the reaction mixture in the form of a pharmaceutically acceptable salt. The pharmaceutically acceptable salts may also be obtained by treating the free base of formula I with an organic or inorganic acid such as HCl, HBr, HI, $H_2SO_4$, $H_3PO_4$, acetic acid, propionic acid, glycolic acid, maleic acid, malonic acid, methanesulphonic acid, fumaric acid, succinic acid, tartaric acid, citric acid, benzoic acid, and ascorbic acid.

The compounds of the invention may be administered parenterally, and for humans preferably in a daily dosage of 0.01–50 mg (preferably 0.1–5 mg) per kg body weight. Mixed with pharmaceutically suitable liquids, e.g. as described in the standard reference, Gennaro et al., Remington's Pharmaceutical Sciences, (18th ed., Mack Publishing Company, 1990, see especially Part 8: Pharmaceutical Preparations and Their Manufacture), the compounds may be processed to an injection preparation in the form of a solution or suspension. Addition salts of compound I may also be obtained by combining a pharmaceutically acceptable salt with an aqueous solution of the compound of formula I under aseptic conditions, whereby the acid addition salt is formed in situ.

The pharmaceutical preparations may further be stabilized by the addition auxiliaries such as pharmaceutically acceptable buffer system, which buffers in the range of pH 3–5. Examples of suitable buffer systems are acetic acid/sodium acetate, citric acid/sodium citrate, and citric acid/disodium phosphate buffers.

The invention is further illustrated by the following examples.

EXAMPLE 1 a) To a stirred solution of 40 g of $(2\beta,3\alpha,5\alpha,16\beta)$-3-hydroxy-2,16-di-(1-piperidinyl)-androstan-17-one in 160 ml of dichloromethane were added 13.5 ml of acetylchloride at 15°–20 ° C. The solution was stirred for 6 h at room temperature and thereafter evaporated to dryness. The residue was dissolved in toluene, the solution again evaporated to dryness and the residue dissolved in dichloromethane. The solution was washed with saturated aqueous sodium carbonate solution, with water and with saturated brine, dried over sodium sulphate, and evaporated to dryness to give 43.5 g of $(2\beta,3\alpha,5\alpha,16\beta)$-3-acetyloxy-2,16-di-(1-piperidinyl)androstan-17-one. Mp 154° C.

b) This product was dissolved in 435 ml of methanol and 125 ml of tetrahydrofuran, after which 15 g of sodium borohydride was added with stirring at a temperature below 15° C. The mixture was stirred at ambient temperature for another 2 h, after which the excess of sodium borohydride was destroyed by carefully adding water. The yellow precipitate was isolated by filtration and washed with water. The solid was dissolved in dichloromethane and the solution was washed with water and brine, dried and evaporated to dryness to give a gum, which was crystallised from acetone to give 19 g of $(2\beta,3\alpha,5\alpha,16\beta,17\beta)$-2,16-di-(1-piperidin-yl)-androstan-3,17-diol 3-acetate. Mp 183 ° C., $[\alpha]_D^{20} = +39.4°$ (c 1.17, chloroform).

c) A solution of 6.6 ml of propionyl chloride in 20 ml of dichloromethane was added dropwise to a stirred solution of 29.5 g of $(2\beta,3\alpha,5\alpha,16\beta,17\beta)$-2,16-di-(1-piperidinyl)-androstan-3,17-diol 3-acetate in 250 ml of dichloromethane and left at room temperature for 20 h. The solution was evaporated to dryness and the residue was dissolved in dichloromethane. The solution was washed with ice-cold, saturated aqueous sodium carbonate solution and with water, dried, evaporated, and chromatographed over alumina to give 26 g of $(2\beta,3\alpha,5\alpha,16\beta,17\beta)$-2,16-di-(1-piperidinyl)-androstane-3,17-diol 3-acetate 17-propionate as a gum. $[\alpha]_D^{20} = -12.7°$ (c 1.01, chloroform).

d) 14 g of methyl bromide were added to a solution of 12.5 g of $(2\beta,3\alpha,5\alpha,16\beta,17\beta)$-2,16-di-(1-piperidinyl)-androstane-3,17-diol 3-acetate 17-propionate in 150 ml of dichloromechane and the solution was set aside at room temperature. After 48 h the solution was evaporated to give crude product as a gum. The product was purified by a combination of chromatography on alumina and crystallisation from dichloromethane-acetone to give 10 g of 1-[$(2\beta,3\alpha,5\alpha,16\beta,17\beta)$-3-(acetyloxy)-17-(1-oxopropoxy)-2-(1-piperidinyl)-androstane-16-yl]-1-methylpiperidinium bromide. Mp 212° C.; $[\alpha]_D^{20} = -12.3°$ (c 1.9, chloroform).

EXAMPLE 2

In a similar manner as described in Example 1, was prepared 1-[$(2\beta,3\alpha,5\alpha,16\beta,17\beta)$-3-(acetyloxy)-17-(1-oxopropoxy)-2-(1-piperidinyl)-androstane-16-yl]-1-(2-propenyl)-piperidinium bromide by using allyl bromide in step d): 15 ml of allyl bromide were added to a solution of 12.5 g of $(2\beta,3\alpha,5\alpha,16\beta,17\beta)$-2,16-di-(1-piperidinyl)-androstane-3,17-diol 3-acetate 17-propionate in 150 ml of dichloromethane and the solution was set aside at room temperature. After 76 h the solution was evaporated to give crude product as a gum. The product was purified by a combination of chromatography on alumina and crystallisation from diethyl ether-acetone to give 9.2 g of 1-[$(2\beta,3\alpha,5\alpha,16\beta,17\beta)$-3-(acetyloxy)-17-(1-oxopropoxy)-2-(1-piperidinyl)- androstane-16-yl]-1-(2-propenyl)piperidinium bromide. Mp 184° C.; $[\alpha]_D^{20} = -12.7°$ (c 1.01, chloroform).

EXAMPLE 3

The following injection preparations were prepared:

| a. The compound of Example 1 | 20 mg |
|---|---|
| citric acid | 10 mg |
| sodium citrate | 4 mg |
| dextran T40 | 20 mg |
| sodium chloride | 3,5 mg |
| water | to 1 mg |
| The components were dissolved in the water and brought to pH 3,8 with NaOH or phosphoric acid. | |
| b. The compound of Example 2 | 20 mg |
| citric acid | 10 mg |
| sodium citrate | 4 mg |
| mannitol | 25 mg |
| water | to 1 mg |
| The components were dissolved in the water and brought to pH 3,8 with NaOH or phosphoric acid. | |
| c. The compound of Example 2 | 20 mg |
| citric acid | 8,3 mg |
| disodium phosphate | 6,5 mg |
| dextran T40 | 20 mg |
| water | to 1 mg |
| The components were dissolved in the water and brought to pH 4,6 with NaOH or phosphoric acid. | |

EXAMPLE 4

The compounds of this invention were compared with pancuronium bromide and vecuronium bromide, using the method described by Marshall et al., Br. J. Anaesth. (1983), 55, 703–714.

| Compound | onset (min) | recovery (min) | duration (min) |
|---|---|---|---|
| pancuronium bromide | 4.1 | 4.0 | 11.7 |
| vecuronium bromide | 4.3 | 2.9 | 10.1 |
| example 1 | 2.3 | 2.9 | 9.0 |
| example 2 | 1.8 | 1.5 | 4.9 | onset = time taken from injection to maximum (approx. 90%) twitch block.
recovery = time from 25-75% recovery of twitch.
duration = time from drug injection to 90% recovery of twitch.

The compounds of the invention are approx. twice as rapid in onset of action compared to pancuronium bromide and vecuronium bromide. In addition, for the compound of example 2, the duration is less than half of the known compounds.

We claim:

1. A monoquaternary 2,16-bispiperidinylandrostane derivative having the formula:

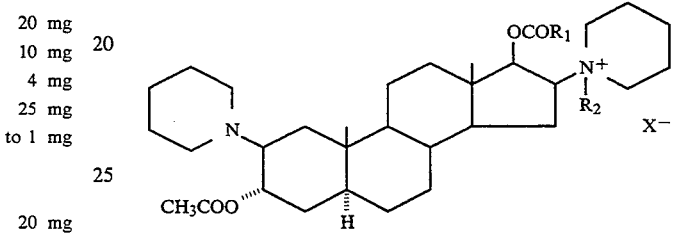

wherein
$R_1$ is ethyl;
$R_2$ is methyl or allyl; and
$X^-$ is a pharmaceutically acceptable anion; or a pharmaceutically acceptable salt thereof.

2. The monoquaternary 2,16-bispiperidinylandrostane derivative of claim 1, wherein $R_1$ is ethyl, $R_2$ is allyl and X is a pharmaceutically acceptable anion; or a pharmaceutically acceptable salt thereof.

3. The monoquaternary 2,16-bispiperidinylandrostane derivative of claim 1, wherein X is $Br^-$.

4. A pharmaceutical composition comprising an effective amount of the monoquaternary 2,16-bispiperidinylandrostane derivative of claim 1 to effect neuromuscular blocking activity and a pharmaceutically acceptable diluent or auxiliary.

5. A method for effecting neuromuscular blocking activity in a patient comprising administering an effective amount of the monoquaternary 2,16-bispiperidinylandrostane derivative of claim 1 to the patient.

* * * * *

UNITED STATES PATENT AND TRADEMARK OFFICE
CERTIFICATE OF CORRECTION

PATENT NO. : 5,418,226

DATED : May 23, 1995

INVENTOR(S) : Thomas Sleigh, Ian C. Carlyle and Alan W. Muir

It is certified that error appears in the above-indentified patent and that said Letters Patent is hereby corrected as shown below:

On the title page, item [56] References Cited:

Please add the following references to the "References Cited" section:

--                FOREIGN PATENT DOCUMENTS 032611        7/1981        European Pat. Off.

008824        3/1980        European Pat Off.

OTHER DOCUMENTS

W.C. Bowman et al., *Chemical Abstracts*, 111:7, Abstract No. 49923, "Pharmacology of Some New Aminosteroid Neuromuscular Blocking Drugs,", Columbus, OH, USA

*Farmakol. Toksikol*, 52:3:29-33, 1989, Moscow (CIS).

A. Muir et al., *Anesthesiology*, Vol. 70:3:533-540, March 1989, USA. "Comparison of the Neuromuscular Blocking and Autonomic Effects of Two new Short-acting Muscle Relaxants with those of Succinylcholine in the Anesthetized Cat and Pig."

UNITED STATES PATENT AND TRADEMARK OFFICE
CERTIFICATE OF CORRECTION

PATENT NO. : 5,418,226
DATED : May 23, 1995
INVENTOR(S) : Thomas Sleigh, Ian C. Carlyle and Alan W. Muir It is certified that error appears in the above-indentified patent and that said Letters Patent is hereby corrected as shown below:

B. Cason et al., *Anesthesia and Analgesia*, 70:4:381-388, April 1990, "Cardiovascular Effects of Three Steroidal Neuromuscular Blocking Drugs in Dogs (ORG-9616, ORG-9426, ORG-9991). --

Signed and Sealed this

Twelfth Day of September, 1995

Attest:

BRUCE LEHMAN

Attesting Officer  Commissioner of Patents and Trademarks